(12) United States Patent
Engelbart et al.

(10) Patent No.: US 7,039,485 B2
(45) Date of Patent: May 2, 2006

(54) SYSTEMS AND METHODS ENABLING AUTOMATED RETURN TO AND/OR REPAIR OF DEFECTS WITH A MATERIAL PLACEMENT MACHINE

(75) Inventors: Roger W. Engelbart, St. Louis, MO (US); Michael R. Chapman, Federal Way, WA (US); Brice A. Johnson, Federal Way, WA (US); Kathryn A. Soucy, Seattle, WA (US); Reed Hannebaum, Mount Vernon, IL (US); Steve Schrader, Bridgeton, MO (US)

(73) Assignee: The Boeing Company, Chicago, IL (US)

( * ) Notice: Subject to any disclaimer, the term of this patent is extended or adjusted under 35 U.S.C. 154(b) by 222 days.

(21) Appl. No.: 10/799,306

(22) Filed: Mar. 12, 2004

(65) Prior Publication Data

US 2005/0203657 A1   Sep. 15, 2005

(51) Int. Cl.
*G06F 19/00* (2006.01)
*B32B 31/00* (2006.01)
(52) U.S. Cl. .................. 700/110; 700/117; 156/379
(58) Field of Classification Search ................ 700/110, 700/117; 382/149; 156/379
See application file for complete search history.

(56) References Cited

U.S. PATENT DOCUMENTS

| | | |
|---|---|---|
| 3,879,245 A | 4/1975 | Fetherson et al. |
| 4,064,534 A | 12/1977 | Chen et al. |
| 4,310,132 A | 1/1982 | Robinson et al. |
| 4,548,859 A | 10/1985 | Kline et al. |
| 4,608,220 A | 8/1986 | Caldwell et al. |
| 4,693,678 A | 9/1987 | Von Volkli |
| 4,699,683 A | 10/1987 | McCowin |
| 4,760,444 A | 7/1988 | Nielson et al. |
| 4,780,262 A | 10/1988 | Von Volkli |
| 4,790,898 A | 12/1988 | Woods |
| 4,830,298 A | 5/1989 | Van Blunk |
| 4,877,471 A | 10/1989 | McCowin et al. |
| 4,941,182 A * | 7/1990 | Patel .......................... 382/141 |
| 5,024,399 A | 6/1991 | Barquet et al. |
| 5,058,497 A | 10/1991 | Bishop et al. |
| 5,337,647 A | 8/1994 | Roberts et al. |

(Continued)

FOREIGN PATENT DOCUMENTS

EP    1 030 172    8/2000

(Continued)

OTHER PUBLICATIONS

U.S. Appl. No. 10/068,735, entitled Composite Material Collation Machine and Associated Method for High Rate of Composite Materials, filed Feb. 6, 2002, Engelbart et al.

(Continued)

*Primary Examiner*—Leo Picard
*Assistant Examiner*—R Jarrett
(74) *Attorney, Agent, or Firm*—Harness Dickey & Pierce P.L.C.

(57) ABSTRACT

A method generally includes electronically accessing positional data defining a defect location on a composite structure, and automatically causing a material placement machine to return to the defect location as defined by the positional data. The method can also include automatically causing the material placement machine to place or lay down material sufficient for repairing a defect at the defect location. Alternatively, the material placement machine may automatically return to a defect location, and then an operator may manually repair the defect at the defect location.

39 Claims, 13 Drawing Sheets

U.S. PATENT DOCUMENTS

| | | | |
|---|---|---|---|
| 5,439,549 | A | 8/1995 | Fryc et al. |
| 5,450,147 | A | 9/1995 | Dorsey-Palmateer |
| 5,518,208 | A | 5/1996 | Roseburg |
| 5,540,126 | A | 7/1996 | Piramoon |
| 5,651,600 | A | 7/1997 | Dorsey-Palmateer |
| 5,683,646 | A | 11/1997 | Reiling, Jr. |
| 5,700,337 | A | 12/1997 | Jacobs et al. |
| 5,746,553 | A | 5/1998 | Engwall |
| 5,804,276 | A | 9/1998 | Jacobs et al. |
| 5,814,386 | A | 9/1998 | Vasiliev et al. |
| 5,825,495 | A | 10/1998 | Huber |
| 5,871,117 | A | 2/1999 | Protasov et al. |
| 5,917,588 | A | 6/1999 | Addiego |
| 5,963,660 | A | 10/1999 | Koontz et al. |
| 5,979,531 | A | 11/1999 | Barr et al. |
| 6,012,883 | A | 1/2000 | Engwall et al. |
| 6,013,341 | A | 1/2000 | Medvedev et al. |
| 6,045,651 | A | 4/2000 | Kline et al. |
| 6,074,716 | A | 6/2000 | Tsotsis |
| 6,086,696 | A | 7/2000 | Gallagher |
| 6,112,792 | A | 9/2000 | Barr et al. |
| 6,168,358 | B1 | 1/2001 | Engwall et al. |
| 6,205,239 | B1 * | 3/2001 | Lin et al. ............ 382/149 |
| 6,364,250 | B1 | 4/2002 | Brinck et al. |
| 6,369,492 | B1 | 4/2002 | Sugimoto |
| 6,390,169 | B1 | 5/2002 | Johnson |
| 6,451,152 | B1 | 9/2002 | Holmes et al. |
| 6,480,271 | B1 | 11/2002 | Cloud et al. |
| 6,648,273 | B1 | 11/2003 | Anast |
| 6,692,681 | B1 | 2/2004 | Lunde |
| 6,725,123 | B1 | 4/2004 | Denuell |
| 6,799,619 | B1 * | 10/2004 | Holmes et al. ............ 156/358 |
| 6,814,822 | B1 * | 11/2004 | Holmes et al. ............ 156/64 |
| 6,871,684 | B1 * | 3/2005 | Engelbart et al. ............ 156/361 |
| 2001/0002149 | A1 | 5/2001 | Vaez-Iravani et al. |
| 2001/0023349 | A1 | 9/2001 | Van Tassel et al. |
| 2002/0141632 | A1 | 10/2002 | Engelbart et al. |

FOREIGN PATENT DOCUMENTS

| | | |
|---|---|---|
| JP | 2001012930 | 1/2001 |
| WO | WO 94/18643 | 8/1994 |

OTHER PUBLICATIONS

U.S. Appl. No. 10/217,805, entitled System for Identifying Defects in a Composite Structure, filed Aug. 13, 2002, Engelbart et al.

U.S. Appl. No. 10/628,691, entitled Systems and Methods for Identifying Foreign Objects and Debris (FOD) and Defects During Fabrication of a Composite Structure, filed Jul. 28, 2003, Engelbart et al.

U.S. Appl. No. 10/664,148, entitled Composite Material Collaboration Machine and Associated Method for High Rate Collation of Composite Materials; divisional application of U.S. Appl. No. 10/068,735, filed Sep. 17, 2003, Engelbart et al.

U.S. Appl. No. 10/726,099, entitled Systems and Methods for Determining Defect Characteristics of a Composite Structure, filed Dec. 2, 2003, Engelbart et al.

Sharp et al.; "*Material Selection/Fabrication Issues for Thermoplastic Fiber Placement*", Journal of Thermosplastic Composite Materials, vol. 8; Jan. 1995, p. 2-14.

U.S. Appl. No. 10/301,949, entitled Parallel Configuration Composite Material Fabricator, filed Nov. 22, 2002, Engelbart et al.

U.S. Appl. No. 10/630,594, entitled Composite Fuselage Machine, filed Jul. 28, 2003, Braun.

U.S. Appl. No. 10/646,316, entitled Unidirectional Multihead Fiber Placement, filed Aug. 22, 2003, New.

U.S. Appl. No. 10/646,392, entitled Composite Lay-Up to an Internal Fuselage Mandrel, filed Aug. 22, 2003, Engwall.

U.S. Appl. No. 10/646,509, entitled Multiple Head Automated Composite Laminating Machine for the Fabrication of Large Barrel Section Components, filed Aug. 22, 2003, Johnson.

U.S. Appl. No. 10/717,030, entitled Method of Transferring Large Uncured Composite Laminates, filed Nov. 18, 2003, Johnson.

http://www.cinmach.com/WolfTracks4_1/MTG_WT7. htm; Premier I Features Lighter, Stronger All-Composite Fuselage, 3 pages.

http://www.cinmach.com/compnews/PressReleases/pr00-11.htm; Raytheon Aircraft Orders Four More Fiber Cincinnati Fiber Placement Systems for Industry's First Composite-Fuselage Business Jets, 2 pages.

http://www.rockymountaincomposites.com/wind_sys.htm; Filament Winding, 2 pages.

U.S. Appl. No. 10/822,538, entitled Systems and Methods for Using Light to Indicate Defect Locations on a Composite Structure, filed Mar. 12, 2004, Engelbart et al.

U.S. Appl. No. 10/846,974, entitled Systems and Methods for Identifying Foreign Objects and Debris (FOD) and Defects During Fabrication of a Composite Structure, filed May 14, 2004, Engelbart et al.

U.S. pending application No. (*not yet assigned*) entitled Composite Barrel Sections for Aircraft Fuselages and Other Structures, and Methods and Systems for Manufacturing Such Barrel Sections, May 20, 2004, Biornstad.

Fiedler, L., et al, "Tango Composite Fuselage Platform", SAMPE Journal, vol. 39, No. 1, Jan./Feb. 2003, pp. 57-63.

BAe 146, Flight International, May 2, 1981, 2 pages.

A Barrelful of Experience, Intervia, May 1992, 2 pages.

Raytheon, Mar. 2000, vol. 4, No. 2, http://www.cts.com/king/vasci/newsletter/vol42.html.

Business Aviation, Jun. 7, 2002, http://www.aviationnow.com/avnow/news/channel_busav.jsp?view=story&id=news/btoyo0607.xml.

Beechcraft's Composit Challenge, http://www.aerotalk.com/Beech.cfm.

Evans, Don O., "Fiber Placement", 3 pages, Cincinnati Machine, pp. 477-479.

Patent Abstracts of Japan, vol. 2000, No. 16, May 8, 2001, Japan.

European Search Report, Application No. 04076900.2, dated Dec. 1, 2004, 4 pages.

U.S. Appl. No. 60/559,911, filed Apr. 4, 2004, Johnson et al.

U.S. Appl. No. 60/559,890, filed Apr. 6, 2004, Biornstad et al.

U.S. Appl. No. 10/819,084, Turnmire et al.

U.S. Appl. No. 10/853,075, Johnson et al.

U.S. Appl. No. 10/949,848, filed Sep. 23, 2004, Stulc.

Advanced Technology Tape Laying for Affordable Manufacturing of Large Composite Structures; http://www.cinmach.com/tech/pdf/TapeLayingGrimshaw.pdf; Michael N. Grimshaw, et al; 11 pages.

Fiber Placement; http://www.cinmach.com/tech/pdf/asm_chapter_fp.pdf; Don O. Evans; Cincinnati Machine; 3 pages.

Automated Tape Laying; http://www.cinmach.com/tech/pdf/Grimshaw%20ASM%20Handbook.pdf; Michael N. Grimshaw; Cincinnati Machine; 6 pages.

Raytheon Aircraft's Hawker Horizon Reaches Fuselage Milestone, Raytheon News Release; http://www.beechcraft.de/Presse/2000/100900b.htm; 2 pages.

* cited by examiner

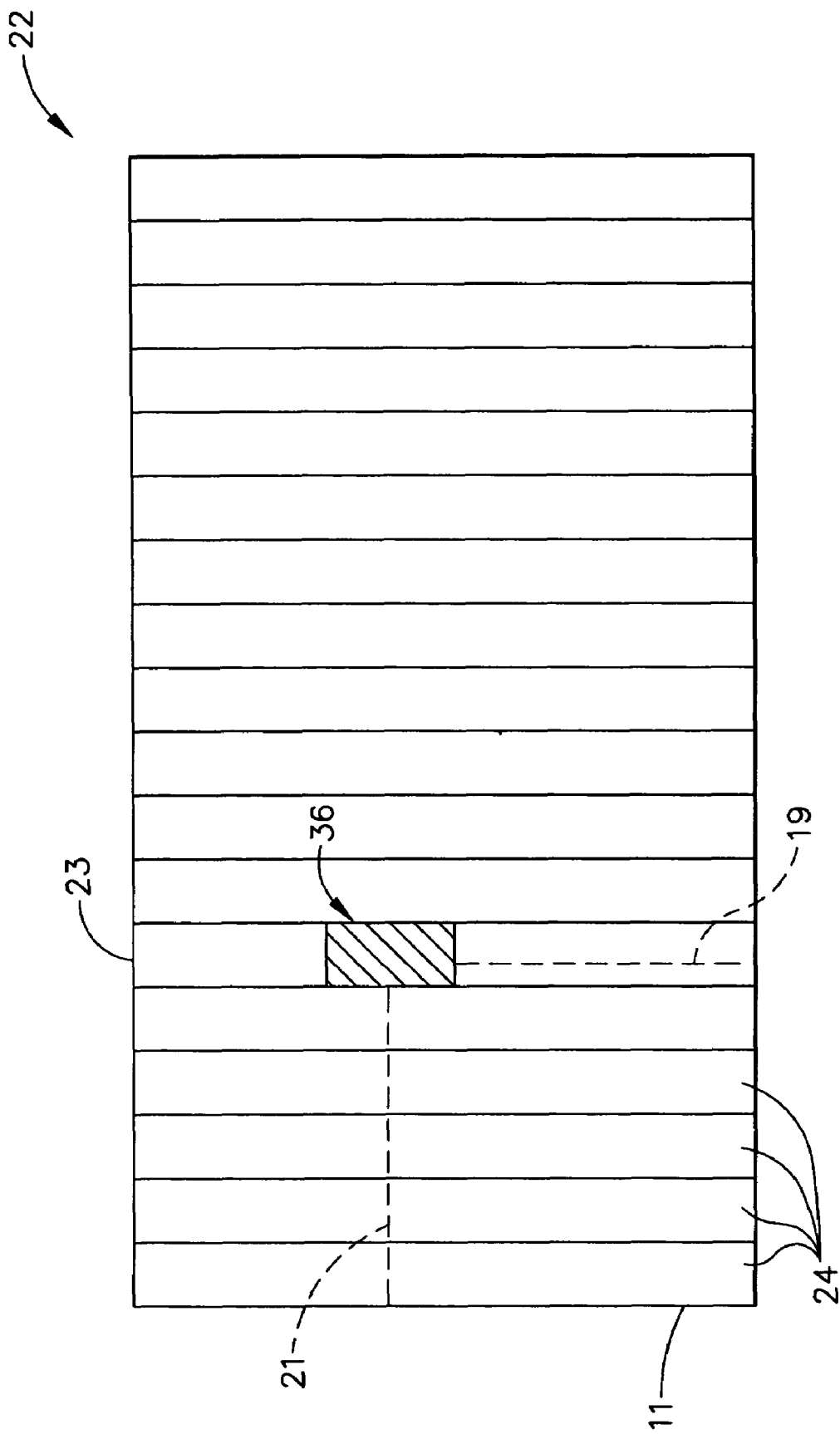

```
N75G67X-21.0014Y24.256Z-40.3284H-.523185H.625822H-.578467D.475303D.77768D.411462 T[ ] L.2105 R.2278$
N76G67X-20.9694Y24.3135Z-40.3008H-.520986H.626242H-.579996D.476623D.777133D.410967 L.0691 R.0748$
N77G67X-20.7996Y24.6094Z-40.1583H-.510021H.627664H-.588147D.482329D.774838D.408639 L.3593 R.3871$
N78G67X-20.5445Y25.0405Z-39.9483H-.495813H.627241H-.600615D.495996D.772242D.397027 L.5235 R.5492$
N79G67X-20.1859Y25.6163Z-39.6704H-.489899H.602916H-.629676D.482231D.789137D.380416 L.7311 R.7653$
N80G67X-19.8706Y26.1118Z-39.4231H-.471868H.602715H-.643487D.494341D.785198D.372949 L.6196 R.6529$
N81G67X-19.5431Y26.6058Z-39.1746H-.455301H.599345H-.658396D.494171D.785243D.372308 L.6296 R.6666$
G64.4X-32.7956Y44.051Z-39.1746H-.455301H.599345H-.658396D.494171D.785243D.37308 F400$
G64.3X-46.0181Y29.9728Z-41.489H-.837935H.54577H0D.54577D.837935D0 F400$
G64.5X-53.549Y12.1877Z-43.8034H-.085443H.019665H-.288119D.956602D.043597 F400$
N1Q21.00G66.32X-24.3552Y5.4685Z-43.8034H-.085443H.019665H-.288119D.956602D.043597 T[ ] F200{}$
N2G67X-24.4574Y5.8076Z-43.788H-.085193H.020711H-.996149D-.276369D.960062D.043597 L.3321 R.3772$
N3G67X-24.556Y6.1503Z-43.7724H-.084932H.021755H-.996149D-.264575D.963379D.043597 L.3343 R.3794$
N4G67X-24.6511Y6.4967Z-43.7568H-.084658H.022793H-.996149D-.25275D.966549D.043596 L.3364 R.3816$
N5G67X-24.7427Y6.8466Z-43.741H-.084371H.023829H-.996149D-.240891D.969573D.043596 L.3386 R.3839$
N6G67X-24.8305Y7.2001Z-43.7251H-.084072H.024862H-.99615D-.228993D.972451D.043597 L.3407 R.3861$
```

109

→ Retract and Approach motion between courses.

FIG. 4

SYSTEMS AND METHODS ENABLING AUTOMATED RETURN TO AND/OR REPAIR OF DEFECTS WITH A MATERIAL PLACEMENT MACHINE

COPYRIGHT NOTICE

A portion of the disclosure of this document contains material that is subject to copyright protection. The copyright owner has no objection to the facsimile reproduction by anyone of the patent disclosure, as it appears in the U.S. Patent and Trademark Office patent files or records, but otherwise the copyright owner reserves all copyright rights whatsoever.

FIELD

The present invention relates generally to the fabrication of composite structures with material placement machines, and more particularly (but not exclusively) to systems and methods that enable a material placement machine to automatically return to defects for manual defect repair, and/or that enable the machine to automatically return to and repair defects without operator intervention.

BACKGROUND

Composite structures have been known in the art for many years. Although composite structures can be formed in many different manners, one advantageous technique for forming composite structures is a fiber placement or automated collation process. According to automated collation techniques, one or more ribbons of composite material (also known as composite strands or tows) are laid down on a substrate with a material placement machine. The substrate may be a tool or mandrel, but, can also be formed of one or more underlying layers of composite material that have been previously laid down and compacted.

Fiber placement processes typically utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. To complete the part, additional strips of composite material can be applied in a side-by-side manner to form layers and can be subjected to localized heat and pressure during the consolidation process.

Unfortunately, defects can occur during the placement of the composite strips onto the underlying composite structure. Such defects can include tow gaps, overlaps, dropped tows, puckers (i.e., raised regions in a tow), and twists. In addition, there are foreign objects and debris (FOD), such as resin balls and fuzz balls, that can accumulate on a surface of the composite structure which must be detected, identified and eventually removed from the ply surface.

Composite structures fabricated by automated material placement methods typically have specific maximum allowable size requirements for each flaw, with these requirements being established by the production program. Production programs also typically set well-defined accept/reject criteria for maximum allowable number of (i.e., density) of defects-per-unit area and maximum allowable cumulative defect width-per-unit area.

To ensure that the composite laminates fabricated by fiber placement processes satisfy the requirements pertaining to defect size, the structures are typically subjected to a 100% ply-by-ply visual inspection. These inspections are traditionally performed manually during which time the fiber placement machine is stopped and the process of laying materials halted until the inspection and subsequent repairs, if any, are completed. In the meantime, the fabrication process has been disadvantageously slowed by the manual inspection process and machine downtime associated therewith.

Recently, systems and methods have been developed that are capable of detecting, measuring, and marking individual defects in the composite structure. Exemplary systems and methods capable of accurately and reliably detecting, measuring and/or marking defects in a composite structure are disclosed in U.S. patent application Ser. No. 09/819,922, filed Mar. 28, 2001, entitled "System and Method for Identifying Defects in a Composite Structure"; U.S. patent application Ser. No. 10/217,805, filed Aug. 13, 2002, entitled "System for Identifying Defects in a Composite Structure"; and U.S. patent application Ser. No. 10/628,691, filed Jul. 28, 2003, entitled "Systems and Methods for Identifying Foreign Objects and Debris (FOD) and Defects During Fabrication of a Composite Structure." The entire disclosures of U.S. patent application Ser. Nos. 09/819,922, 10/217,805, and 10/628,691 are each incorporated herein by reference as if fully set forth herein.

Systems and methods have also been developed which are capable of determining a defect characteristic representative of the composite structure, such as a defect density-per-unit area and/or cumulative defect width-per-unit area. Exemplary systems and methods capable of determining defect characteristics are disclosed in U.S. patent application Ser. No. 10/726,099, filed Dec. 2, 2003, entitled "Systems and Methods for Determining Defect Characteristics of a Composite Structure", the contents of which are incorporated herein by reference as if fully set forth herein.

While the above-mentioned inspection systems and methods have worked well for their intended purposes and have reduced unproductive down time associated with inspection of laminate plies, the inventors hereof have recognized that repair of detected flaws is still very much a manual, labor-intensive process.

SUMMARY

The present invention relates to systems and methods that enable a material placement machine to automatically return to defects which may then be manually repaired and/or that enable the material placement machine to automatically return to and repair defects without operator intervention.

In a preferred implementation, a method generally includes electronically accessing positional data defining a defect location on a composite structure, and automatically causing a material placement machine to return to the defect location as defined by the positional data. The method can also include automatically causing the material placement machine to place or lay down material sufficient for repairing a defect at the defect location. Alternatively, the material placement machine may automatically return to a defect location, and then an operator may manually repair the defect at the defect location.

In another preferred implementation, a program generally includes a plurality of inputs for enabling the program to access positional data defining a defect location. The program also includes a module for automatically generating instructions in connection with the inputs. The instructions automatically cause a material placement machine to return to the defect location as defined by the positional data. The program can also include a module for automatically causing the material placement machine to place material sufficient for repairing a defect at the defect location. Alternatively, the material placement machine may automatically return to a defect location, and then an operator may manually repair the defect at the defect location.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein:

FIG. 1 is a schematic view of an exemplary composite structure illustrating linear and lateral distances to a defect in the composite structure;

FIG. 4 illustrates an exemplary block of NC code for generating corresponding retract and approach motions of the material placement machine between courses;

DETAILED DESCRIPTION OF THE PREFERRED EMBODIMENTS

Figure 2A:
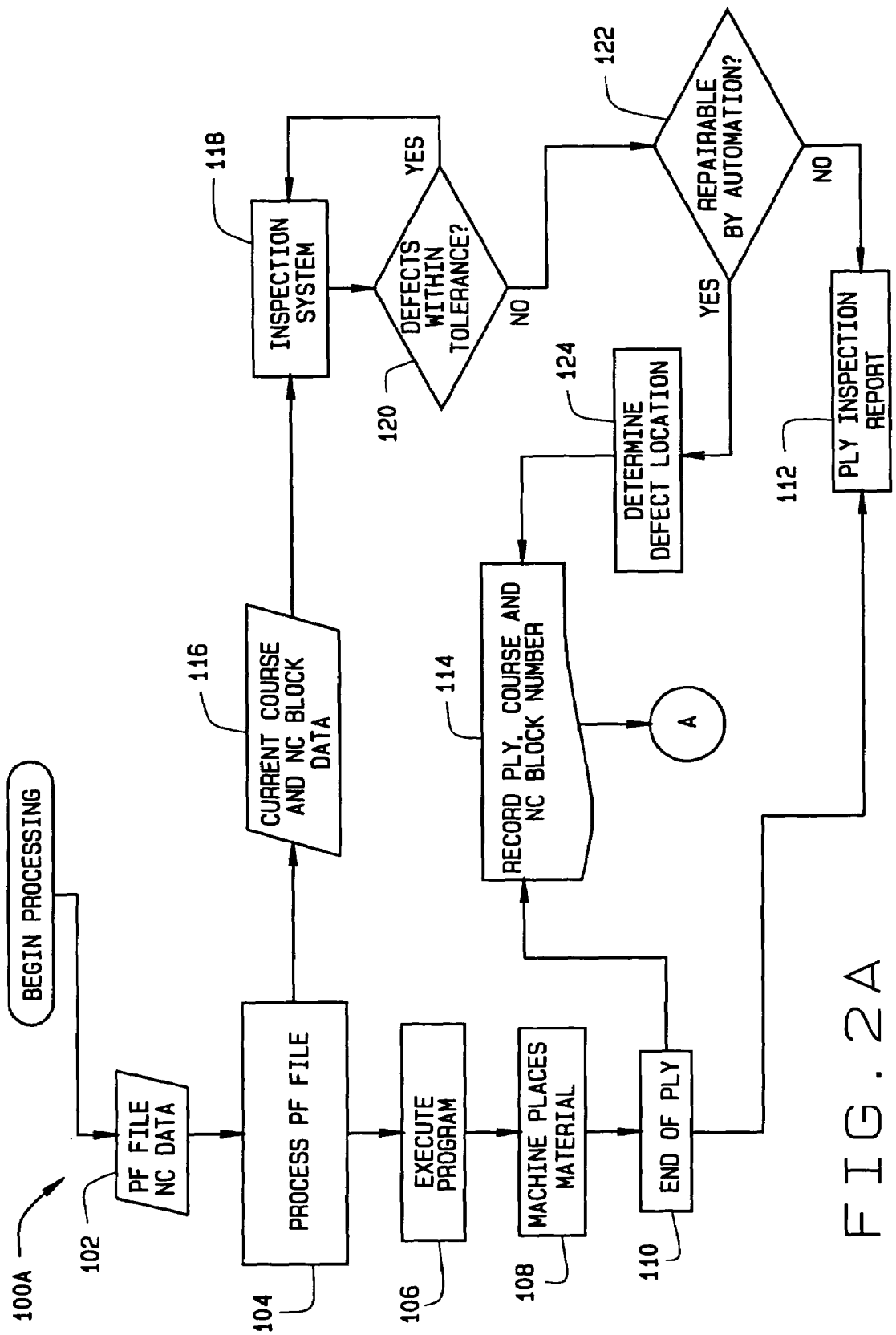
FIGS. 2A and 2B form a process flow diagram illustrating operations of a method enabling automated repair of defects with a material placement machine according to a preferred implementation.

The following description of the preferred embodiments is merely exemplary in nature and is in no way intended to limit the invention, its application, or uses.

According to one aspect, the invention provides systems and methods enabling a material placement machine to automatically return to defects for manual defect repair and/or to automatically return to and repair defects without operator intervention. In a preferred implementation, a method generally includes electronically accessing positional data defining a defect location on a composite structure, and automatically causing a material placement machine to return to the defect location as defined by the positional data. In various implementations, the method can also include automatically causing the material placement machine to place or lay down material sufficient for repairing a defect at the defect location. Alternatively, the material placement machine may automatically return to a defect location, and then an operator may manually repair the defect at the defect location. After completion of the manual repair, the motion of the material placement machine may then be manually restarted or controlled by the operator, for example, to cause the material placement machine to move to another defect location.

According to another aspect of the invention, a program generally includes a plurality of inputs for enabling the program to access positional data defining a defect location. The program also includes a module for automatically generating instructions in connection with the inputs. The instructions automatically cause a material placement machine to return to the defect location as defined by the positional data. In various implementations, the program can include a module for automatically causing the material placement machine to place material sufficient for repairing a defect at the defect location. Alternatively, the material placement machine may automatically return to a defect location, and then an operator may manually repair the defect at the defect location. After completion of the manual repair, the motion of the material placement machine may then be manually restarted or controlled by the operator, for example, to cause the material placement machine to move to another defect location.

Although aspects of the present invention can be described with a program having a direct effect on and direct control of the material placement machine, it should be understood that it is the instructions generated by executing a program, for example by a processor in communication with the material placement machine, and the subsequent implementation of such instructions by the processor, that have direct effect on and direct control of the material placement machine.

By way of example only, FIG. 1 illustrates an exemplary composite structure 22 which can include a plurality of layers or plies. Each ply is generally comprised of a plurality of adjacent tows or strips of composite tape 24. The strips 24 typically include a plurality of fibers embedded in a resin or other material that becomes tacky or flowable upon the application of heat. The strips 24 can be arranged on a work surface, such as a table, mandrel, or other tool 26 (FIG. 6), and compacted with a compaction roller 20 (FIG. 7) to form the composite structure 22 according to an automated collation technique, such as that described in U.S. patent application Ser. No. 10/068,735, filed on Feb. 6, 2002, entitled "Composite Material Collation Machine and Associated Method for High Rate Collation of Composite Materials". The contents of U.S. patent application Ser. No. 10/068,735 are incorporated herein by reference in its entirety as if fully set forth herein.

As shown in FIG. 1, eighteen courses or strips 24 have been completed by the material placement machine. That is, the material placement machine has made eighteen passes across a substrate. During each of the passes, the material placement machine has laid down a strip 24 on the substrate. The sixth course 23 of the composite structure 22 includes a defect 36 where a portion of a tow is missing. The dashed line 19 represents the linear distance along the sixth course 23 to the defect 36. The dashed line 21 represents the lateral distance to the defect 36 from a first end 11 of the composite structure 22.

Figure 2B:
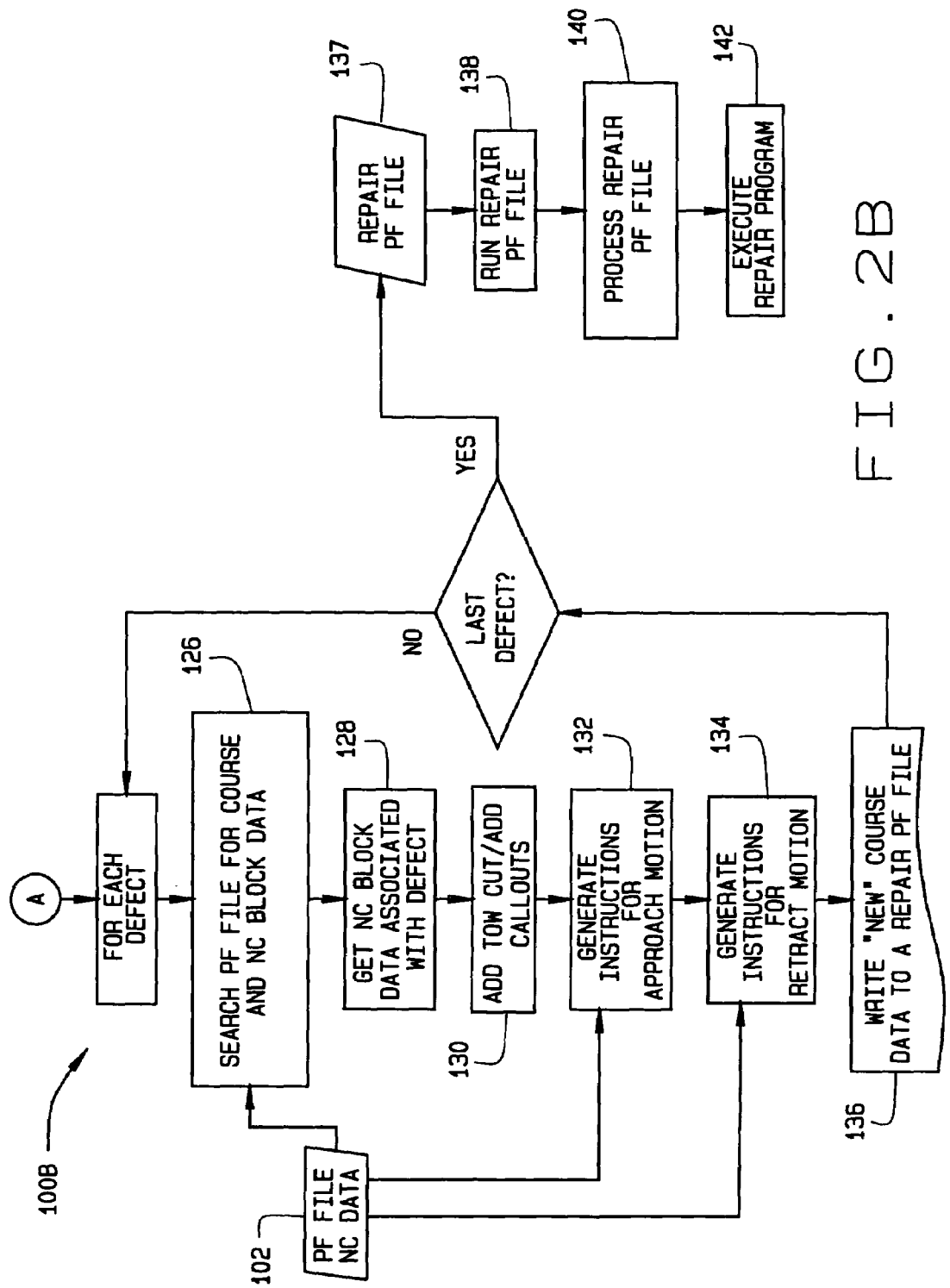

FIGS. 2A and 2B form a process flow diagram illustrating operations of a method 100 enabling in-process repair of defects during fabrication of a composite structure with a material placement machine according to a preferred implementation. As shown in FIG. 2A, the method can include intelligent front end (IFE) processing of a part fabrication file 102 at operation 104. The part fabrication file 102 can include data and information for the material placement machine to fabricate the composite structure from start to finish. Exemplary information within the file 102 can include numerical control (NC) data defining the various approach and retract motions for the material placement machine and information defining the part specifications such as perimeter, size, contour, etc.

Figure 3:
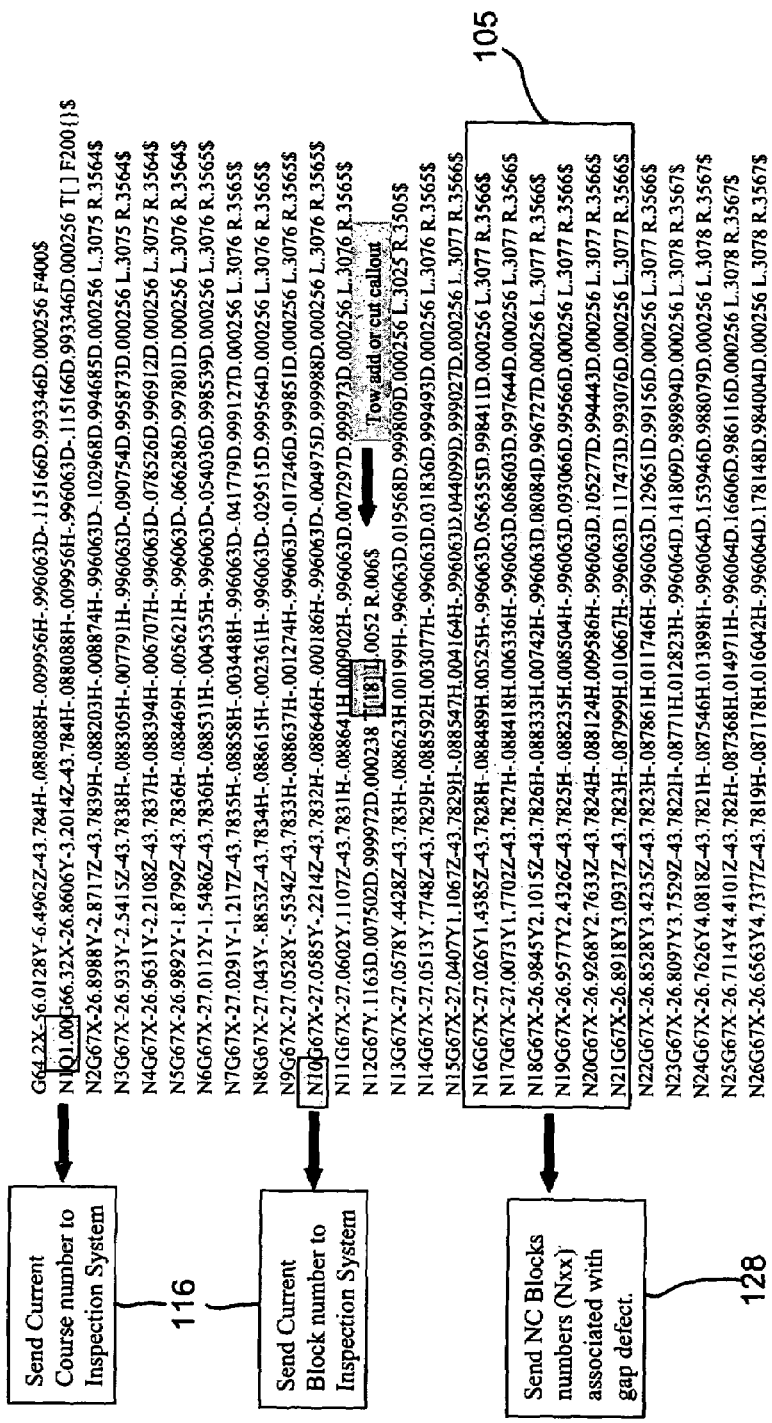
FIG. 3 illustrates an exemplary block of numerical control (NC) data within a part fabrication file for a material placement machine.

FIG. 3 illustrates an exemplary block of numerical control (NC) data 103 that may be included within a part fabrication file 102 for a particular type of material placement machine. FIG. 3 illustrates various lines of data reflecting the material placement machine's location and its operation at a specific point and time. FIG. 3 also illustrates a block 105 of lines associated with a defect location. FIG. 3 is for purposes of illustration only, and the type and content of program code for the material placement machine can vary depending on the particular application and particular material placement machine being used.

In FIG. 2A, operation 106 includes execution of a program, for example by a processor in communication with the material placement machine. Execution of the program generates the instructions or commands for causing the material placement machine to begin laying or placing the material at operation 108. FIG. 4 illustrates an exemplary block of code 109 for generating the corresponding retract and approach motions of the material placement machine between courses. FIG. 4 is for purposes of illustration only, and the type and content of the program code for the material placement machine will vary depending on the particular application and particular material placement machine being used.

As shown in FIG. 2A, a ply inspection report is created at operation 112 when the material placement machine completes or comes to the end of a ply or layer, as represented by box 110. The ply, the course and the NC block number associated therewith can be logged or recorded at operation 114.

With reference to FIGS. 2A and 3, current course number and current block number 116 can be sent to an inspection system. Operation 118 (FIG. 2A) includes the inspection system inspecting the composite structure for defects. Preferably, this inspection occurs generally concurrently with operation 108 in which the material is being placed by the material placement machine. Exemplary systems and methods capable of detecting defects in a composite structure are described generally below and in more detail in U.S. patent application Ser. No. 09/819,922, filed Mar. 28, 2001, entitled "System and Method for Identifying Defects in a Composite Structure"; U.S. patent application Ser. No. 10/217,805, filed Aug. 13, 2002, entitled "System for Identifying Defects in a Composite Structure"; and U.S. patent application Ser. No. 10/628,691, filed Jul. 28, 2003, entitled "Systems and Methods for Identifying Foreign Objects and Debris (FOD) and Defects During Fabrication of a Composite Structure." The entire disclosures of U.S. patent application Ser. Nos. 09/819,922, 10/217,805, and 10/628,691 are each incorporated herein by reference as if fully set forth herein.

Operation 120 includes determining whether a detected defect is acceptably within certain predefined tolerances or criteria, such as maximum allowable dimensional parameters and tolerances as established by production program. By way of example only, this determination can be made by counting the number of pixels from a digital image representing the defect and then using that pixel count to compute an indirect quantitative measurement for the defect based upon correlation data including a predetermined relationship between pixel count and distance or dimensional limits.

Operation 122 includes determining whether an unacceptable defect (i.e., a defect determined to be unacceptable at operation 120) can be repaired automatically by the material placement machine without requiring manual repair or user intervention. Exemplary types of defect that can be repaired by automation are dropped tows and tow gaps having a width equal to the width of the tow. Information about the defects that are not repairable by automation is logged or recorded in the ply inspection report at operation 112. Exemplary types of defects which may be determined to be incapable of being repaired by automation with the material placement machine can include foreign objects and debris (FOD) and unacceptable/rejected gaps that are narrower than the width of a tow.

The defects which are determined to not be repairable by automation can be marked (as described below) to enable the location of such defects to be readily visible, although such is not required. Additionally, or alternatively, various implementations can also include the material placement machine returning to a defect which has been determined to be irreparable by automation. An operator may then manually repair the defect at the defect location. After completion of the manual repair, the motion of the material placement machine may then be manually restarted or controlled by the operator, for example, to cause the material placement machine to move to another defect location.

Operation 124 includes determining a location for each unacceptable defect that can be repaired by automation with the material placement machine. Additionally, or alternatively, operation 124 can include determining a location for each defect which has been determined to be irreparable by automation.

In preferred implementations, defect locations can be determined by exterior monitoring of the material application/lay-down position of the material placement machine. Exemplary systems and methods capable of determining defect locations are described generally below and in more detail in U.S. patent application Ser. No. 10/726,099, filed Dec. 2, 2003, entitled "Systems and Methods for Determining Defect Characteristics of a Composite Structure", the contents of which are incorporated herein by reference as if fully set forth herein.

The positional data defining the location or coordinates for a defect can be logged, recorded and tracked at operation 114.

With reference now to FIGS. 2B and 3, operation 126 includes searching the part fabrication file 102 (FIG. 2B) for course and NC block data 105 (FIG. 3) associated with a defect. By way of example, the inspection system upon detection of defect can produce a signal which is used to flag or identify the numerical control block data defining the coordinates for that defect's location.

At operation 128, the NC block data 105 associated with the defect is obtained or extracted. Operation 130 includes adding new tow cut and/or tow add commands (e.g., add a tow and cut it to this length). By way of example, execution of the new tow cut/add commands can include actuation of the appropriate cutting knife to deposit an appropriate length of tow and/or to splice in a single tow piece from a band a multiple tows.

Figure 5:
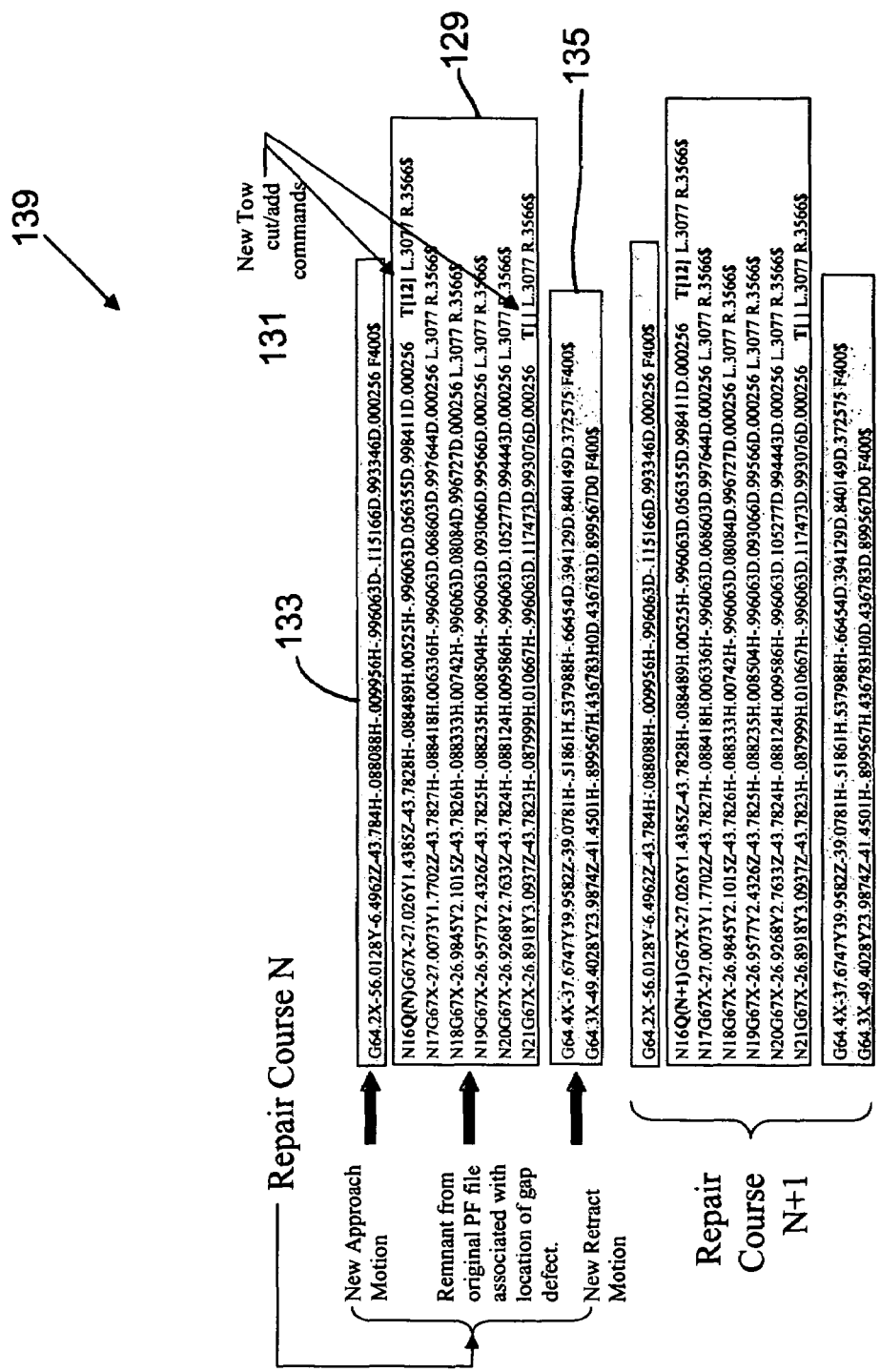
FIG. 5 illustrates an exemplary block of NC code of a repair part fabrication file for causing the material placement machine to return to a defect location and repair the defect at the defect location.

FIG. 5 illustrates a remnant 129 of NC block data associated with a defect, wherein the remnant 129 was extracted from the part fabrication file 102. FIG. 5 further illustrates exemplary new tow cut/add commands 131 added at operation 130. FIG. 5 is for purposes of illustration only, and that the type and content of the program code for the material placement machine will vary depending on the particular application and particular material placement machine being used.

With further reference to FIGS. 2B and 5, operation 132 includes creating instructions or commands 133 for a new approach motion for the material placement machine. Operation 134 includes creating instructions or commands 135 for a new retract motion for the material placement machine. Creating these new or unscheduled approach and retract commands can include accessing the part fabrication file 102. The new motion commands 133 and 135 cause the material placement machine to proceed along a course (i.e., the new approach motion) in which a defect is located, and then retract (i.e., the new retract motion) upon reaching the end of the course. Preferably, the repair code or routines for the material placement machine are automatically written based on NC block information and data from the inspection/vision system.

At operation 136, the "new course" data (e.g., the extracted NC block data 129, new tow cut/add commands 131, and approach and retract commands 133 and 135) are written to a repair part fabrication file 137. FIG. 5 illustrates an exemplary block of numerical control (NC) code 139 that may be included within a repair part fabrication file 137 for a particular type of material placement machine.

Operations 126 through 136 can be repeated for each defect detected by the inspection system (operation 118, FIG. 2A) for which it has been determined is unacceptable (operation 120) and is repairable by automation (operation 122). In various implementations, operations 126 through 136 can also be repeated for each defect determined to be unacceptable (operation 120) and not repairable by automation. In such implementations, an operator may manually repair the defect at the defect location to which the material placement machine has returned. After completion of the manual repair, the motion of the material placement machine may then be manually restarted or controlled by the operator, for example, to cause the material placement machine to move to another defect location. The number of times that operations 126 through 136 are repeated will depend on the number of such defects.

With further reference to FIG. 2B, operation 138 can include running the repair part fabrication file 137. Operation 140 can include intelligent front end (IFE) processing of the repair part fabrication file 137.

Operation 142 includes execution of the repair program which causes the material placement machine, after laying the material to complete a ply of the composite structure, to return to a course in which a defect is located and place material along the course sufficient to repair the defect. For example, the material placement machine can return to lay a tow or a portion of a tow that was somehow dropped or missed during the initial lay down.

Typically, a part fabrication file for a new part will not include programming for repairing unacceptable defects because defects usually cannot be predicted with certainty. Instead, the part fabrication file will include what is necessary to make the material placement machine lay the material for forming the part from start to finish. Implementation of the above-described method, however, enables the program code for causing the material placement machine to return to and repair defects to be automatically written.

Accordingly, implementations of the present invention enable automated, in-process repair of defects without the need for machine down time. This, in turn, reduces manufacturing costs and increases machine utilization. Various implementations of the invention allow composite structures to be fabricated more efficiently with fewer interruptions than conventional material placement systems in which repairing defects is still very much a manual, labor-intensive process.

Figure 6:
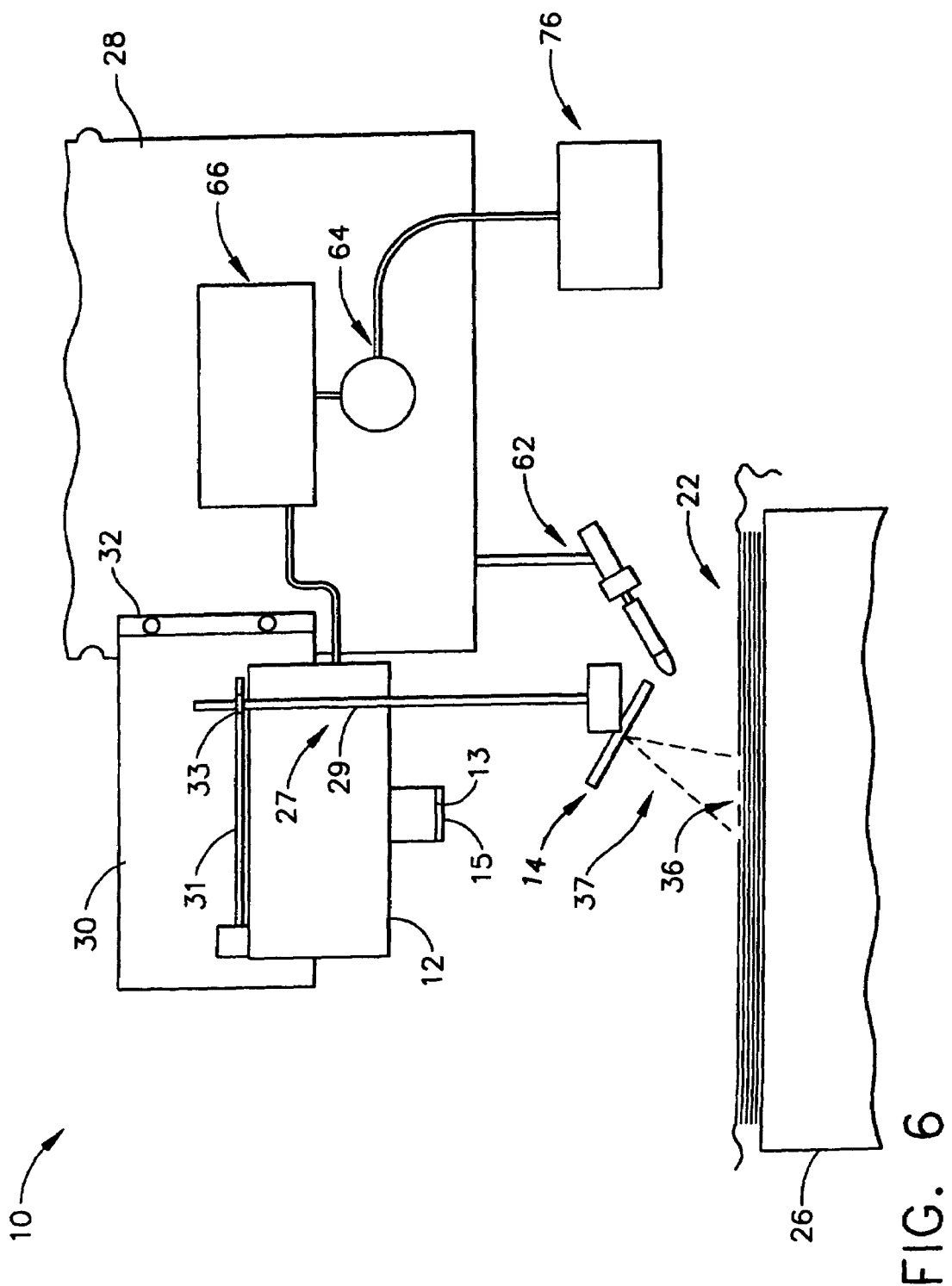
FIG. 6 is a schematic view of an exemplary system for inspecting a composite structure for defects.

An exemplary system 10 which can be used at operation 116 (FIG. 2A) to detect defects in a composite structure is illustrated in FIG. 6. As shown in FIG. 6, the system 10 includes at least one camera 12 and at least one light source 14. The camera 12 is connected to a processor 66 for interpreting the images the camera 12 captures, or to a storage device 64 for storing the images, or both, as discussed more fully below.

The light source 14 is positioned to emit light for illuminating the composite structure 22. The illumination is reflected differently by defects in the composite structure than from portions of the composite structure that are defect free. For example, illumination reflecting off non-defective portions of the composite structure 22, and light that fails to reflect off of defects in the composite structure 22, or vice versa, creates visible images that can be captured by the camera 12. Details regarding systems and methods for identifying defects in a composite structure during fabrication thereof are included in previously referred to U.S. patent application Ser. Nos. 09/819,922, 10/217,805, 10/628,691, and Ser. No. 10/726,099.

Figure 8:
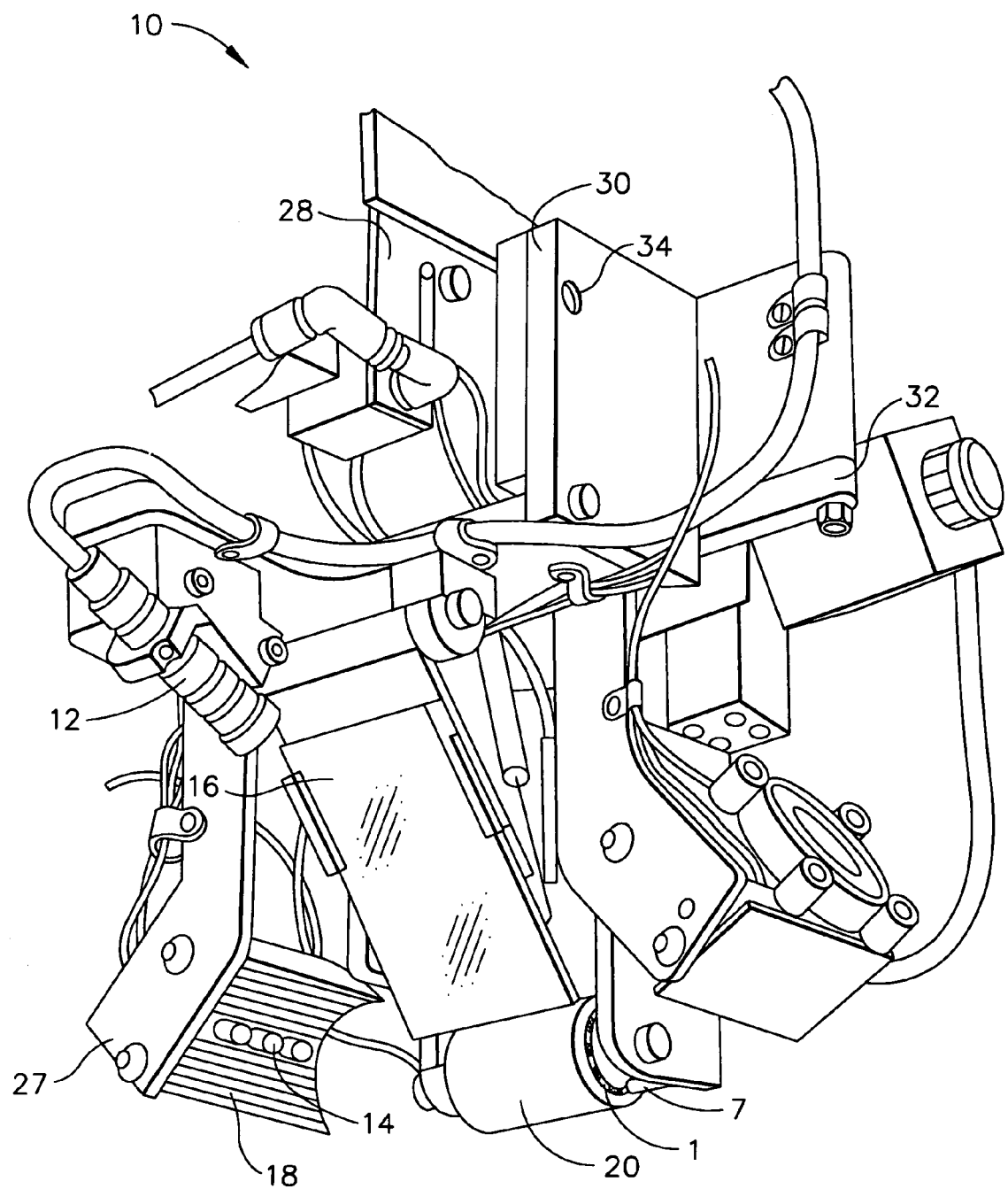
FIG. 8 is a perspective view of another exemplary system for inspecting a composite structure for defects.

As shown in FIG. 6, the camera 12 is positioned near the composite structure 22 so as to capture images of portion of the composite structure being illuminated, which is typically immediately downstream of the nip point at which a composite tow is joined with the underlying structure. Alternatively, and as shown in FIG. 8, a reflective surface 16 may be positioned near the composite structure (the composite structure is not shown in FIG. 8), and angled such that the reflective surface 16 reflects an image of the illuminated portion of the composite structure. The camera 12 may be positioned to point toward the reflective surface 16 in order to capture close-range images of the illuminated portion of the composite structure from the reflective surface 16. More than one reflective surface 16 may also be utilized in further embodiments of the invention in which the reflective surfaces 16 cooperate in order to direct images of the illuminated portion of the composite structure to the camera 12.

A wide range of cameras can be used including commercially-available cameras capable of acquiring black and white images. In one embodiment, the camera 12 is a television or other, type of video camera having an image sensor (not shown) and a lens 13 (FIG. 6) through which light passes when the camera 12 is in operation. Other types of cameras or image sensors can also be used, such as an infrared-sensitive camera, a visible light camera with infrared-pass filtration, a fiber optic camera, a coaxial camera, Charge Coupled Device (CCD), or Complementary Metal Oxide Sensor (CMOS). The camera 12 can be positioned proximate the composite structure 22 on a stand (not shown) or mounted to a frame 28 or similar device.

In those embodiments that do not include a reflective surface 16, the camera 12 may be mounted to the frame 28 by way of a bracket 30 and associated connectors 32, as shown in FIG. 6. The connectors 32 may be rivets, screws or the like that mount the camera 12 to the frame 28 in a stationary position. Alternatively, the connectors 32 may be a hinge-type connector that permits the camera 12, light source 14, and associated assembly to be rotated away from the composite structure 22. This embodiment is advantageous in situations where other parts of the material placement device, particularly the parts located behind the camera 12 and associated assembly, must be accessed, such as for maintenance, cleaning, or the like.

FIG. 8 illustrates an alternative embodiment of the hinge-type connector 32 that mounts the camera 12, reflective surface 16, light source 14, and associated assembly (e.g., camera assembly) to the frame 28 by way of a bracket 30. A suitable fastener, such as a thumbscrew or any other fastener that may be removed or loosened with relative ease, can be inserted through hole 34 and then tightened to secure the camera assembly in place for operation. The fastener may be loosened or removed, for example, to rotate the camera assembly away from the compaction roller 20 and other parts of the fiber placement device.

With further reference to FIG. 6, a filter 15 can be placed on the lens 13 for filtering light in a particular manner. In one embodiment, the filter 15 is designed to filter light such that only the infrared component or a certain infrared wavelength or range of wavelengths of light can pass into the camera 12. In this manner, the filter 15 prevents ambient visible light from entering the camera 12 and altering the appearance of the captured image.

Other methods of filtering light can also be used to achieve the same, or at least similar, result. For example, the camera may be designed to include a built-in filter of equivalent optical characteristics. In addition, the filter can be located between the camera lens 13 and image sensor. Alternatively, the camera may include an image sensor that is only sensitive in the infrared spectrum (e.g., an infrared-sensitive camera), thus eliminating the need for the filter.

The light source 14 of the system 10 will now be described in more detail. The light source 14 is positioned to emit light for illuminating at least a portion of the composite structure 22.

In FIG. 6, the light source 14 is shown positioned at an oblique angle 37 relative to the composite structure 22. The oblique angle 37 may be about forty-five degrees, although other angles are possible depending on the application. In addition, the light source 14 is also shown positioned to emit light in a direction substantially perpendicular to the direction of placement of the strips 24 in order to highlight the defects 36, as described below.

Figure 10:
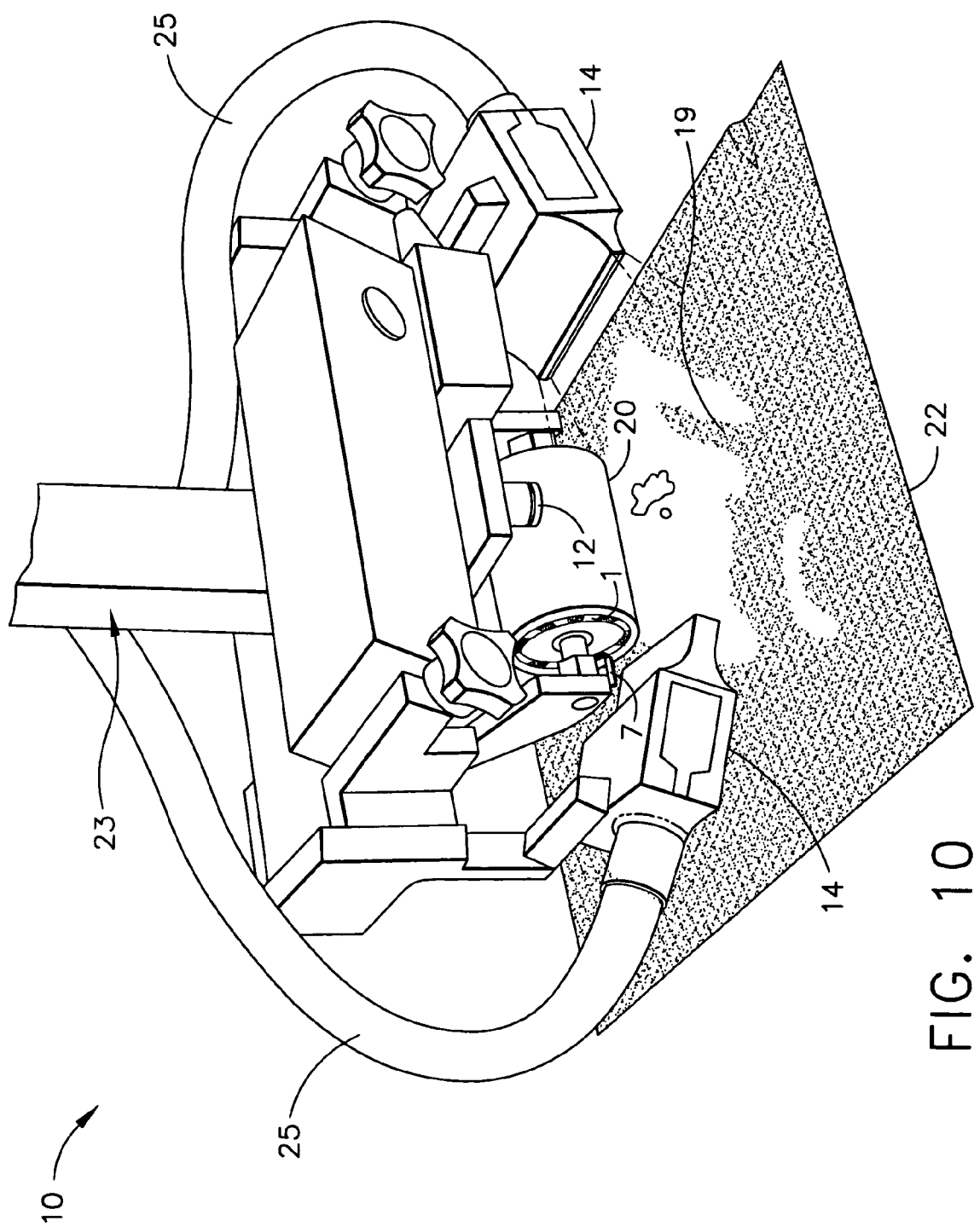
FIG. 10 is a perspective view of another exemplary system for inspecting a composite structure for defects.

Further, the system 10 may include more than one light source. For example, the embodiment of FIG. 8 includes two light sources 14 positioned relative to the composite structure and compaction roller 20 on either side of the reflective surface 16 and camera 12. Another exemplary embodiment that includes two light sources 14 is shown in FIG. 10 in which two linear optical fiber arrays are positioned on opposed sides of the camera 12.

In FIG. 6, the light source 14 is adjustably positioned relative to the composite structure 22 by mounting or attaching the light source 14 to a mounting apparatus 27. The mounting apparatus 27 can include a main shaft 29, a secondary shaft 31, and a locking clamp 33 for quickly and accurately adjusting the position of the light source 14. The mounting apparatus 27, in turn, can be attached to the frame 28, to the camera 12, to the bracket 30, or to some other object that defines a common position for both the light source 14 and the camera 12 such that the light source 14 and camera 12 maintain a constant spatial relationship relative to one another.

The quality and magnitude of the surface illumination of the composite structure can be affected by ambient lighting and by reflectivity of the material. Accordingly, embodiments of the invention advantageously employ an infrared light source to more effectively illuminate dark flaws on a dark background. In this regard, the light source 14 can be selected from an infrared light or another type of light having an infrared component, such as a halogen light source (FIG. 9) or other incandescent light sources (not shown). In other embodiments, the light source 14 can also include a fluorescent light source (e.g., white light LEDs, low pressure/mercury filled phosphor glass tube, etc.), a strobe or stroboscopic light source, a noble gas arc lamp (e.g., xenon arc, etc.), metal arc lamp (e.g., metal halide, etc.) and a lasers (e.g., pulsed lasers, solid state laser diode arrays, infrared diode laser arrays, etc.). The light from the light source 14 may also be pumped from through optical fibers to the point of delivery, such as is shown in FIG. 10.

In some embodiments, the light source 14 is operated at a power level that maximizes, or at least significantly increases, the infrared (IR) component of the light which works well for inspecting dark tow material, such as carbon. In this regard, exemplary power levels in the range of up to about one hundred fifty watts (150 W) in the wavelength range of about seven hundred nanometers to eleven hundred nanometers (700 nm–1100 nm) have been sufficient. However, the particular power levels and wavelengths for the light source will likely depend at least in part on the camera's speed and sensitivity, speed at which the material is being laid, delivery losses, and reflectivity of the material being inspected, among other factors. For example, in other embodiments, wavelengths and power levels suitable for inspecting highly reflective materials can be employed.

In the embodiment shown in FIG. 6, the light source 14 may comprise a plurality of LEDs arranged in an array or cluster formation. In one specific embodiment, the light source 14 includes 24 LEDs mounted in an array upon a three-inch square printed circuit board.

Figure 9:
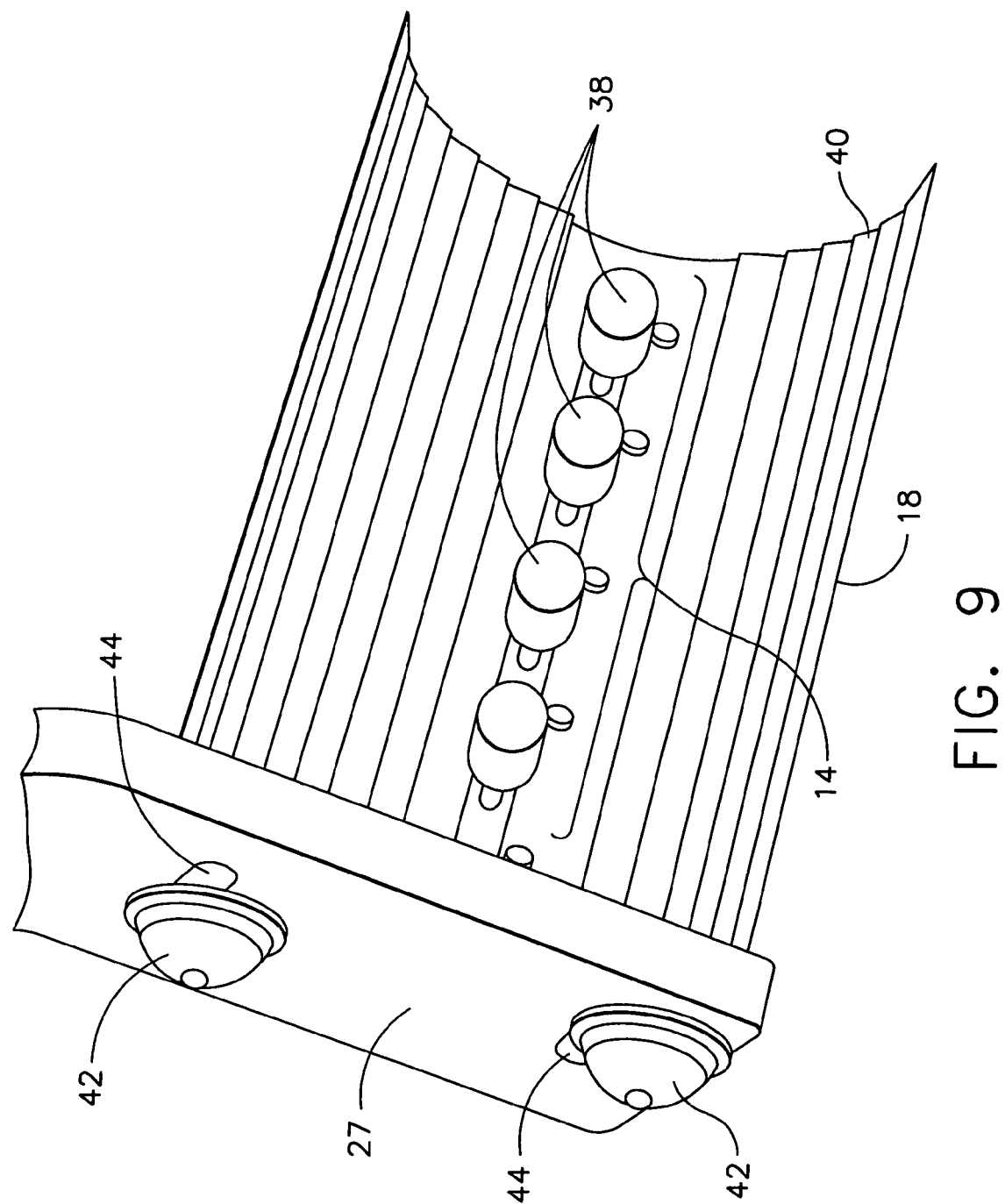
FIG. 9 is a perspective view of a light source according to the system embodiment shown in FIG. 8.

In another embodiment shown in FIGS. 8 and 9, the light source 14 includes four halogen light bulbs 38, although other quantities can and have also been used.

Figure 11:
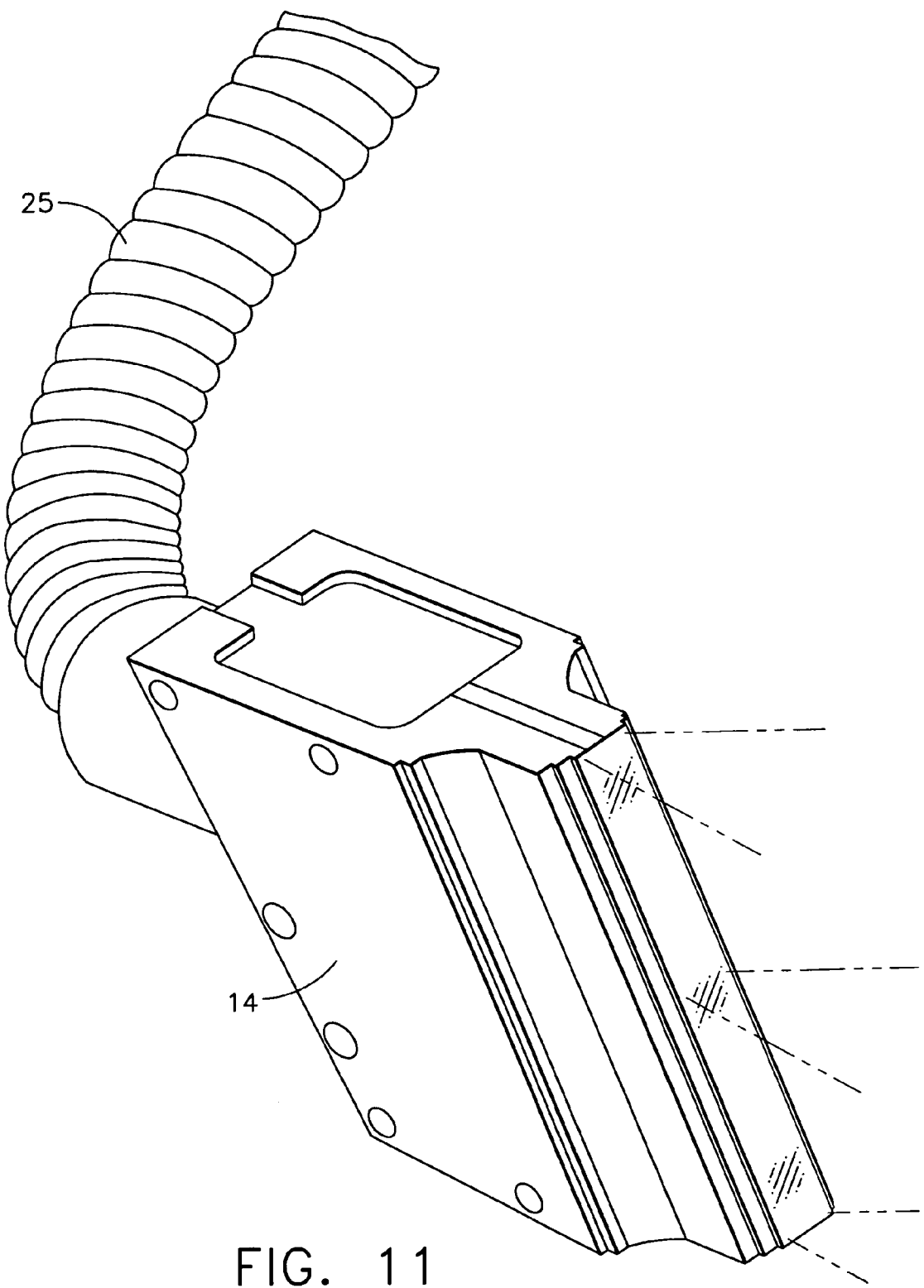
FIG. 11 is a perspective view of a light source according to the system embodiment shown in FIG. 10.

In the embodiment shown in FIG. 10, the light source 14 includes two linear optical fiber arrays positioned on opposite sides of the camera 12. The arrays emit light supplied from a remote source (not shown) through an optical fiber bundle 25. An illuminated linear array 14 is shown in FIG. 11.

Referring back to FIG. 8, the system 10 may further include a light reflection element 18 located near the light source 14. The reflection element 18 includes a series of light reflecting surfaces 40 (FIG. 9) that redirect the light towards the desired area to be illuminated. This levels the illumination across the surface and eliminates, or at least substantially reduces, areas of intense light (i.e., hotspots) created by the brightest portion of the light source 14. Hotspots are undesirable because hotspots can prevent consistent illumination of the composite structure, which may lead to errors during the processing of the images captured by the camera 12.

The light reflection elements 40 are particularly advantageous for illuminating curved/contoured surfaces of composite structures because the redirection of the light permits a larger portion of the composite structure to be evenly illuminated.

As shown in FIG. 9, the reflection element 18 is curved around the light source 14, such as in a parabolic shape. On the surface of the reflection element 18 that faces the light source 14, the reflection element 18 includes curved steps 40 substantially parallel to the light source 14. The distance between and curvature of the steps 40 can be chosen to be sufficient to provide even illumination from the sum of the two light sources, one on either side of the region of interest.

This enables the reflection element 18 to provide more consistent illumination of the composite structure 22, which prevents, or at least reduces, image processing errors due to inconsistent illumination of the composite structure 22. Alternatively, the shape and/or surface configuration of the reflection element 18 can be modified in other ways that also produce consistent illumination and scattering of the light produced by the light source 14 over the desired portion of the composite structure 22.

In an exemplary embodiment, the reflection element 18 has an overall parabolic shape with seventeen parabolic curved steps 40 having a range of widths from about 0.125 inches at the outer edge of the reflection element 18 to about 0.250 inches at the center of the reflection element 18. The reflection element 18 also has a uniform step height of about 0.116 inches. In other embodiments, however, the reflection element may be provided with different numbers of steps having different uniform or varying widths and different uniform or varying step heights.

Furthermore, the reflection element 18 may be adjusted in order to direct the light produced by the light source 14 and scattered by the reflection element 18 toward the desired portion of the composite structure. For example, as shown in FIG. 9, the reflection element 18 is adjustably mounted to the mounting apparatus 27 with fasteners 42. The loosened fasteners 42 can move within slots 44 to correspondingly adjust the angle of the reflection element 18 relative to the composite structure. Once the reflection element 18 is positioned appropriately, the fasteners 42 are tightened to secure the reflection element 18 in the desired position. Adjustments of the reflection element 18 can also be enabled by other methods, such as by electronic means that permit remote adjustment of the reflection element 18.

It has been observed that the composite structure 22 can produce high glare when illuminated across the direction of placement of the strips 24 but produces substantially less glare when illuminated along the direction of placement of the strips 24. The systems and methods of at least some embodiments exploit the high-glare/low-glare phenomenon by casting light across the top layer of the composite strips 24 in a direction substantially perpendicular to the direction of placement of the strips 24. This produces a relatively large amount of glare on the top layer of the composite structure 22. The underlying layers, which produce significantly less glare than the top layer because of their orientation, will show through any gaps or other defects in the top layer and thus be easily located. In addition, twists and other surface defects in the top layer will alter the orientation of the strips in the top layer and thus correspondingly alter, i.e., decrease, the glare of the top layer at the defect location.

While the high-glare/low-glare phenomenon can occur when illuminated with either visible light or infrared light, the filter 15 used in one embodiment of the system 10 substantially removes the glare caused by ambient light such that only the glare caused by the infrared light source is used to locate the defects. Accordingly, the filter 15 removes the interference of ambient light as the composite structure 22 is being examined for defects.

In any of the system embodiments described herein, there may be one or more cameras 12 and/or one or more light sources 14 with or without reflection elements 18 (collectively referred to as light sources, hereinafter). In addition, the one or more cameras 12 and/or the one or more light sources 14 may be moveable relative to the composite structure. The multiple cameras 12 and/or multiple light sources 14 and the moveability of the camera(s) 12 and/or the light source(s) provides system 10 flexibility in order to capture the most accurate images of the composite structure. Multiple and/or moveable light source(s) 14 permit consistent and sufficient illumination of the desired portion of the composite structure, regardless of the shape of the composite structure. Likewise, multiple and/or moveable camera(s) 12 enable capturing an accurate image of any area of the composite structure, regardless of the shape of the composite structure. As such, the multiple and/or moveable light source(s) and/or camera(s) are particularly advantageous when illuminating and capturing images of curved/contoured portions of composite structures. The multiple and/or moveable light source(s) and/or camera(s) are also advantageous in illuminating and capturing images of composite strips having a width that makes it difficult to illuminate and/or capture images of the entire strip, such that the position of the light source(s) and/or camera(s) may be moved over the entire strip, and/or multiple stationary light source(s) and/or camera(s) may be positioned to cover the entire strip. Systems including moveable cameras and light sources are described in detail in previously referred to U.S. patent application Ser. No. 10/217,805.

As shown in FIG. 6, the system 10 can also include a marking device 62 for marking the location of defects on the composite structure 22. The marking device 62 may be attached to the frame 28 and be triggered by a processor 66 or similar device when a defect is detected. The marking device 62 may spray or otherwise deposit an amount of ink, paint or the like onto the composite structure 22 in those areas where defects have been detected. The markings on the composite structure 22 enable the location of the defects to be subsequently readily identified either automatically or manually.

In the particular illustrated embodiment, the marking device 62 is an inkjet marking system that sprays a small spot of compatible ink of a highly visible color onto the surface of the composite structure 22 at the defect location to permit rapid access for repair and disposition. Alternatively, other marking methods can also be used, such as a pump-fed felt-tip marker, spring-loaded marking pen, audio or visual alerts, pass/fail indicators on a software interface (e.g., user interface 76, etc.) displayed on a display screen, combinations thereof, and the like.

The camera 12 and/or the reflective surface 16, which along with the light source 14 and any reflection element 18, can be mounted to the head unit to allow the camera 12 to continuously capture real-time images of the composite structure 22 and the strips 24 as the head unit moves across the composite structure 22 and the composite strips 24 are laid down. If the composite structure 22 is not planar, the inspection point should preferably be as close to the nip point as possible, as described above. If the composite structure 22 is planar, the inspection point can be located further from the placement head unit. In either case, the images can be stored in a memory device 64 for future analysis and/or processed immediately by the processor 66.

The processor 66 may receive the images from the camera 12 or from the memory device 64 in which images have been stored. The processor 66 may then process and analyze the images to facilitate the reliable detection of defects. In at least one embodiment, the processor 66 and memory device 64 are components of a conventional computer.

Various methods can be used to determine the defect locations (e.g., linear distance 19 and lateral distance 21 to a defect 36, FIG. 1) at operation 124 (FIG. 2A). Details regarding systems and methods for determining defect locations are included in previously referred to U.S. patent application Ser. No. 10/726,099.

In an exemplary implementation, linear distance to a defect along a course can be determined by multiplying the velocity of the material placement head unit along the course with the amount of time that has lapsed between when the course began and when the defect is detected.

Figure 7:
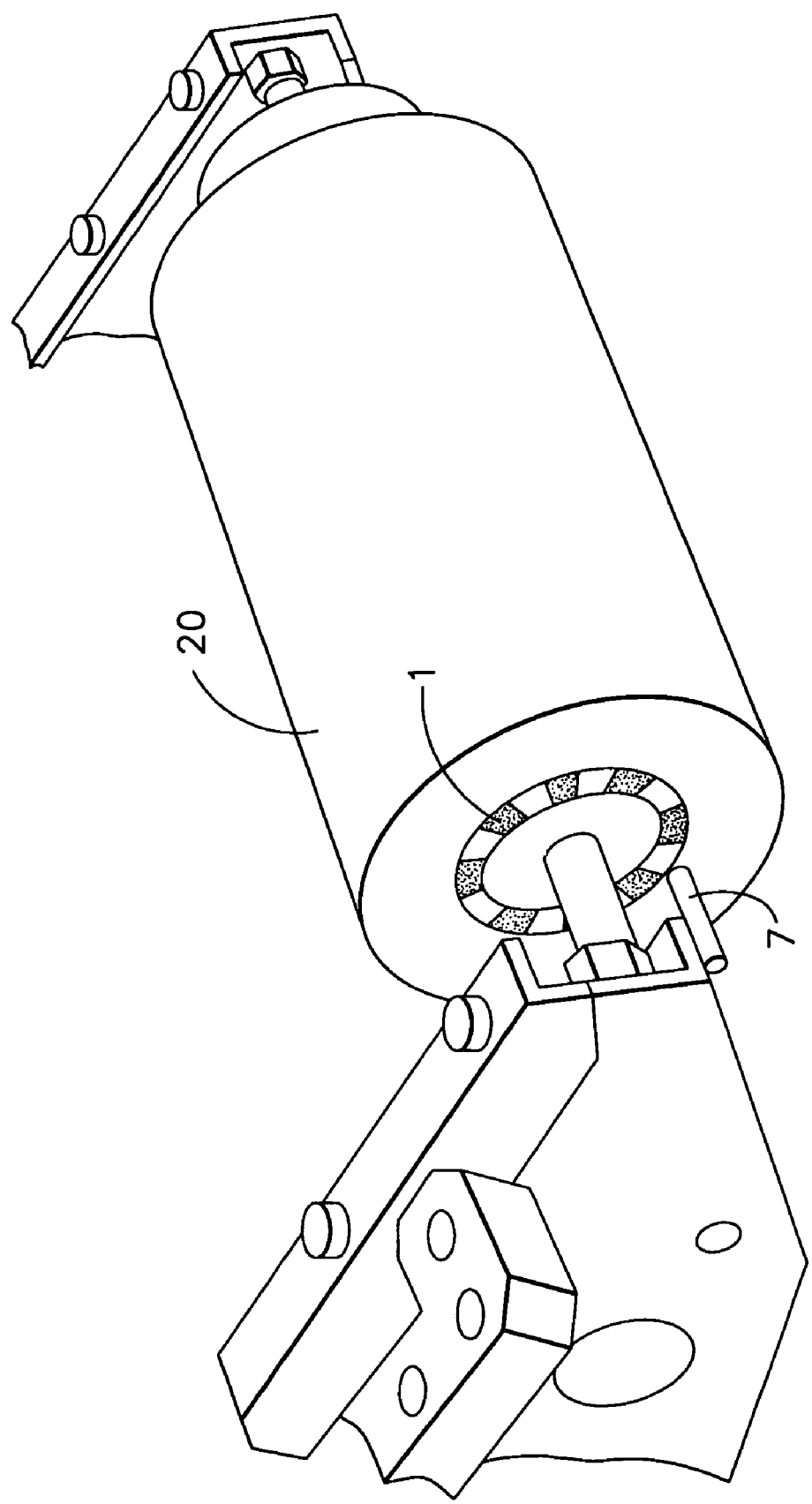
FIG. 7 is a perspective view of an exemplary compaction roller having a code ring coupled thereto for common rotation therewith and a photo sensor positioned to monitor the code ring.

The start and stop of a course can be determined using signals from the machine load cell which indicate whether or not pressure is being applied to the compaction roller 20 (FIGS. 7, 8, and 10). Receipt of a "pressure on" signal from the machine load cell indicates that the compaction roller 20 is in contact with the composite structure 22 and therefore, that a course has been started. Receipt of a "pressure off" signal indicates that the compaction roller 20 is no longer in contact with the composite structure 22, and therefore that a course has been completed. Accordingly, the time between course start and defect detection can be determined by tracking the amount of time elapsing between receipt of the "pressure on" signal from the machine load cell and the receipt of the signal indicating detection of a defect.

Alternatively, course start and stop can be determined by receipt of a signal from a device employing proximity sensors, lasers, or sound detectors positioned for determining whether or not the compaction roller 20 is in contact with the composite structure 22.

In one implementation, velocity of the head unit is determined by determining the angular velocity of the compaction roller 20 and multiplying the angular velocity by a circumference of the compaction roller 20. Alternatively, other methods can also be used to determine the velocity of the head unit, such as by using a radar gun commonly used for law enforcement purposes in monitoring vehicular speeds along roadways.

Figure 12:
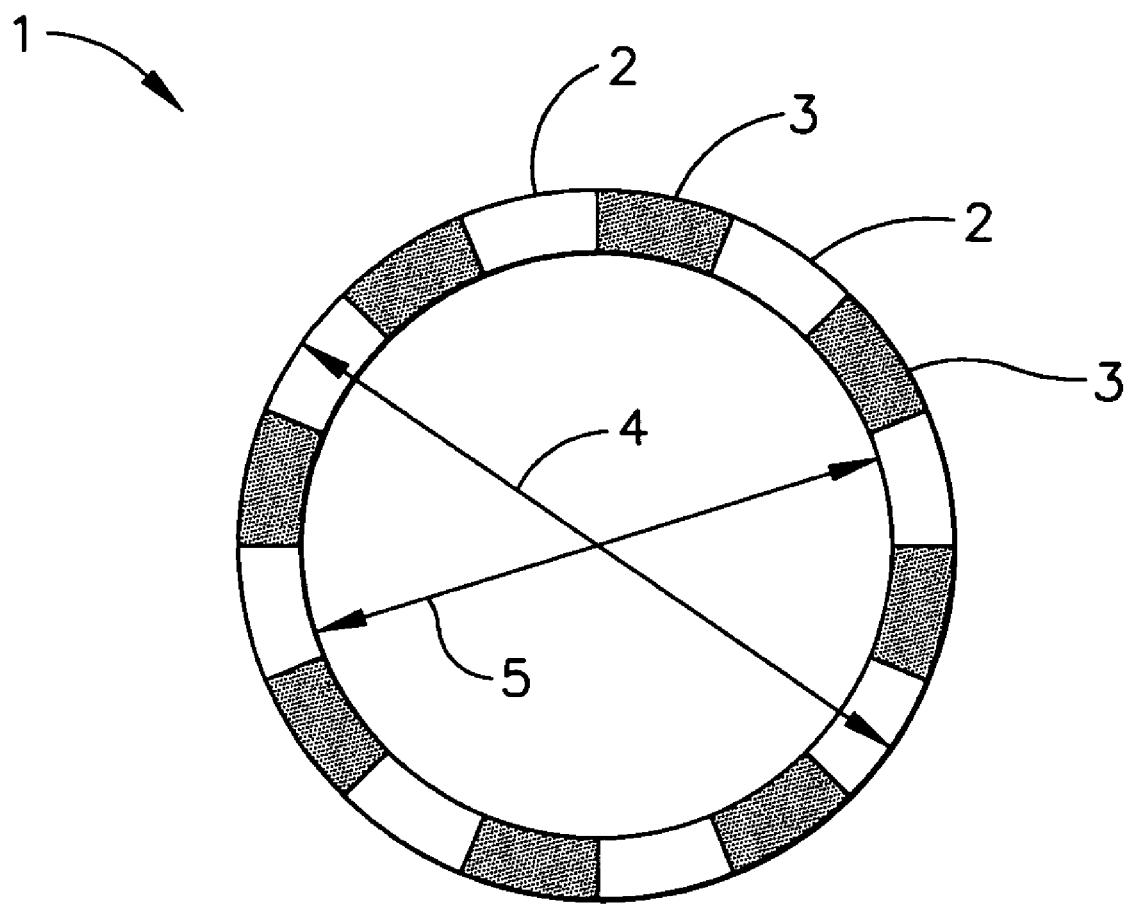
FIG. 12 is a schematic view of the code ring shown in FIG. 7.

Referring to FIGS. 7, 8, and 12, the angular velocity of the compaction roller 20 can be determined by a code ring 1 coupled for common rotation with the compaction roller 20. As shown, the code ring 1 includes alternating contrasting portions 2 and 3, such as alternating black and white segments. In FIG. 12, the code ring 1 includes an outer diameter 4 of about 1.010 inches and an inner diameter 5 of about 0.844 inches, although other ring sizes can also be employed. In other embodiments, the contrasting portions can be provided directly on the compaction roller 20 (e.g., marked on, painted on, etc.), thereby eliminating the need for the separate code ring 1.

With further reference to FIGS. 7 and 8, a photo sensor 7 (e.g., an off-the-shelf photo diode, etc.) is positioned to monitor and capture real-time images of the light-to-dark transitions of the code ring 1 as the code ring 1 rotates along with the compaction roller 20. By detecting and counting the light-to-dark transitions of the ring 1, the compaction roller revolutions can be counted and monitored. The frequency at which the light-to-dark transitions occur can be used to establish the angular velocity of the compaction roller 20. Preferably, axial motion in the compaction roller 20 is minimized in order to maintain the distance from the photo sensor 7 to the code ring 1 constant, which, in turn, allows for more accurate determination of the machine head unit's velocity.

In another exemplary embodiment, the linear distance to a defect along a course can be determined by counting the number (whole and fractional) of revolutions the compaction roller 20 makes from the start of the course to the defect and multiplying that number of revolutions by the circumference of the compaction roller 20. By way of example, the photo sensor 7 and code ring 1 can be used to count the number of revolutions of the compaction roller 20 between receipt of the "pressure on" signal from the machine load cell and receipt of the signal indicating that a defect has been detected.

Various methods can also be employed to determine the lateral distances to defects from the first end 11 of the composite structure 22. See FIG. 1. In one exemplary embodiment, lateral distance to a defect can be calculated by counting the total number of completed courses, not including the course in which the defect resides, and then multiplying the average width of a course by the number of completed courses. This method is particularly effective for tape placement in which each course is the same width, i.e., the width of the tape.

The total number of completed courses can be determined by tracking or counting receipt of the pressure on/off signals from the machine load cell. Receipt of a "pressure on" signal from the machine load cell indicates that the compaction roller 20 is in contact with the composite structure 22 and has thus started a course. Receipt of a "pressure off" signal indicates that the compaction roller 20 is no longer in contact with the composite structure 22 and has thus completed the course.

For fiber placement courses in which the width of each course may not be equal, the lateral distances to defects can be accurately determined by employing a "software ruler." More specifically, the lateral distance can be determined by acquiring a digital image of at least the portion of the composite structure including the lateral distance; selecting a pixel set from the digital image that represents the lateral distance; counting the number of pixels comprising the pixel set; and correlating the pixel count with correlation data (e.g., a predetermined relationship between pixel count and distance) to compute an indirect quantitative measurement for the lateral distance.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method enabling automated repair of defects in a composite structure formed with a material placement machine that lays composite material in one or more courses and one or more plies to form the structure, the method comprising:
    inspecting a course of the composite structure for defects;
    determining whether a defect detected by the inspecting is unacceptable;
    determining whether a defect detected by the inspecting is repairable by the material placement machine without user intervention; and
    automatically causing the material placement machine to return to and place material sufficient for repairing a defect determined to be unacceptable and repairable by the material placement machine without user intervention.

2. The method of claim 1, further comprising automatically causing the material placement machine to return to each defect determined to be unacceptable.

3. The method of claim 1, wherein the automatically causing includes electronically accessing positional data defining a location of a defect.

4. The method of claim 1, wherein the automatically causing includes creating a program to automatically generate instructions for causing the material placement machine to return to and place material sufficient for repairing defects determined to be unacceptable and repairable by the material placement machine without user intervention.

5. The method of claim 1, wherein the method includes communicating with an inspection system performing the inspecting.

6. The method of claim 1, further comprising exterior monitoring of the material application position of the material placement machine to determine a location of a defect detected by the inspecting.

7. A method comprising:
using a material placement machine to lay one or more courses and one or more plies of composite material to form a composite structure;
inspecting the one or more courses for defects;
determining whether a defect detected by the inspecting is unacceptable; and
automatically causing the material placement machine to return to a defect determined to be unacceptable.

8. The method of claim 7, further comprising:
determining whether a defect is repairable by the material placement machine without user intervention; and
automatically causing the material placement machine to return to and place material sufficient for repairing a defect determined to be unacceptable and repairable by the material placement machine without user intervention.

9. The method of claim 7, wherein the automatically causing includes electronically accessing positional data defining a location of a defect.

10. The method of claim 7, wherein the automatically causing includes creating a program to automatically generate instructions for causing the material placement machine to return to a defect determined to be unacceptable.

11. The method of claim 7, wherein the method includes communicating with an inspection system performing the inspecting.

12. The method of claim 7, further comprising exterior monitoring of the material application position of the material placement machine to determine a location of a defect detected by the inspecting.

13. A method comprising:
using a material placement machine to lay one or more courses and one or more plies of composite material to form a composite structure;
electronically accessing positional data defining a defect location on the composite structure; and
automatically causing the material placement machine to return to the defect location as defined by the positional data.

14. The method of claim 13, wherein the automatically causing includes automatically causing the material placement machine to place material sufficient for repairing a defect at the defect location.

15. The method of claim 14, wherein the automatically causing includes automatically causing the material placement machine, after completing a ply of the composite structure, to return to a course of the ply in which a defect is located and place material along the course sufficient for repairing the defect.

16. The method of claim 14, wherein the automatically causing includes creating a program to automatically generate instructions in connection with the positional data, for causing the material placement machine to return to the defect location as defined by the positional data and place material sufficient for repairing the defect at the defect location.

17. The method of claim 16, wherein the program extracts the positional data from a first file to a second file and generates the instructions within the second file.

18. The method of claim 14, further comprising determining whether a defect is repairable by the material placement machine without user intervention, and wherein the automatically causing includes automatically causing the material placement machine to repair a defect determined to be repairable by the material placement machine without user intervention.

19. The method of claim 13, further comprising inspecting the composite structure for defects.

20. The method of claim 13, further comprising exterior monitoring of the material application position of the material placement machine to determine a first distance from a first reference point of the composite structure to a defect.

21. The method of claim 20, wherein the monitoring includes detecting and counting transitions between contrasting portions of a code ring coupled for common rotation with a compaction roller.

22. The method of claim 20, further comprising:
summing courses completed to produce a total completed course count; and
multiplying a predetermined course width by the total completed course count to determine a second distance from a second reference point of the composite structure to the defect.

23. The method of claim 22, wherein summing courses completed includes tracking receipt of signals from a machine load cell indicating whether pressure is being applied to a compaction roller.

24. The method of claim 13, further comprising determining whether a defect is unacceptable, and wherein the automatically causing includes automatically causing the material placement machine to return to a defect determined to be unacceptable.

25. A machine-readable medium for use with a processor having a memory, the machine-readable medium comprising:
instructions to cause the processor to access positional data defining a defect location on a composite structure formed by a material placement machine that lays composite material in one or more courses and one or more plies to form the structure; and
instructions to cause the processor to generate instructions to cause the material placement machine to return to the defect location as defined by the positional data and place material sufficient for repairing the defect at the defect location.

26. The machine-readable medium of claim 25, further comprising instructions to cause the processor to extract positional data from a first file to a second file, the second file including the instructions generated by the processor.

27. The machine-readable medium of claim 25, wherein the processor generates instructions for automatically causing the material placement machine, after completing a ply of the composite structure, to return to a course of the ply in which a defect is located and place material along the course sufficient for repairing the defect.

28. The machine-readable medium of claim 25, wherein the processor generates instructions for automatically causing the material placement machine to repair only defects which are determined to be unacceptable.

29. The machine-readable medium of claim 25, wherein the processor generates instructions for automatically causing the material placement machine to repair only defects which are determined to be repairable by the material placement machine without user intervention.

30. The machine-readable medium of claim 25, further comprising instructions to cause the processor to communicate with an inspection system capable of inspecting the composite structure for defects.

31. The machine-readable medium of claim 25, further comprising instructions to cause the processor to communicate with an inspection system capable of determining a location of a defect by exterior monitoring of the material application position of the material placement machine.

32. A machine-readable medium for use with a processor having a memory, the machine-readable medium comprising:

instructions to cause the processor to access positional data defining a defect location on a composite structure formed by a material placement machine that lays composite material in one or more courses and one or more plies to form the composite structure; and instructions to cause the processor to generate instructions for automatically causing the material placement machine to return to the defect location as defined by the positional data.

33. The machine-readable medium of claim 32, further comprising instructions to cause the processor to extract positional data from a first file to a second file, the second file including the instructions generated by the processor.

34. The machine-readable medium of claim 32, wherein the processor generates instructions for automatically causing the material placement machine to return to only defects which are determined to be unacceptable.

35. The machine-readable medium of claim 32, further comprising instructions to cause the processor to communicate with an inspection system capable of inspecting the composite structure for defects.

36. The machine-readable medium of claim 32, further comprising instructions to cause the processor to communicate with an inspection system capable of determining a location of a defect by exterior monitoring of the material application position of the material placement machine.

37. A method comprising:

electronically accessing positional data defining a defect location on a composite structure;

automatically causing a material placement machine to return to the defect location as defined by the positional data; and performing exterior monitoring of the material application position of the material placement machine to determine a first distance from a first reference point of the composite structure to a defect, the monitoring including detecting and counting transitions between contrasting portions of a code ring coupled for common rotation with a compaction roller.

38. A method comprising:

electronically accessing positional data defining a defect location on a composite structure;

automatically causing a material placement machine to return to the defect location as defined by the positional data;

performing exterior monitoring of the material application position of the material placement machine to determine a first distance from a first reference point of the composite structure to a defect;

summing courses completed to produce a total completed course count; and multiplying a predetermined course width by the total completed course count to determine a second distance from a second reference point of the composite structure to the defect.

39. The method of claim 38, wherein summing courses completed includes tracking receipt of signals from a machine load cell indicating whether pressure is being applied to a compaction roller.

* * * * *